United States Patent [19]
Aida et al.

[11] Patent Number: 5,485,839
[45] Date of Patent: Jan. 23, 1996

[54] METHOD AND APPARATUS FOR ULTRASONIC WAVE MEDICAL TREATMENT USING COMPUTED TOMOGRAPHY

[75] Inventors: Satoshi Aida, Tokyo; Mariko Shibata; Katsuhiko Fujimoto, both of Kanagawa; Yoshiharu Ishibashi, Tokyo; Takuji Suzuki, Kanagawa; Kozo Sato, Kanagawa; Ayao Itoh, Kanagawa, all of Japan

[73] Assignee: Kabushiki Kaisha Toshiba, Kanagawa, Japan

[21] Appl. No.: 300,199

[22] Filed: Sep. 2, 1994

Related U.S. Application Data

[63] Continuation of Ser. No. 22,911, Feb. 26, 1993, abandoned.

[30] Foreign Application Priority Data

Feb. 28, 1992 [JP] Japan ................................. 4-043603
Sep. 11, 1992 [JP] Japan ................................. 4-242886

[51] Int. Cl.$^6$ ................................................... A61B 6/00
[52] U.S. Cl. ..................... 128/653.1; 128/653.2; 128/660.03; 601/2; 601/4
[58] Field of Search ................... 128/653.1, 653.2, 128/660.03; 601/2–4; 607/97

[56] References Cited

U.S. PATENT DOCUMENTS

| | | |
|---|---|---|
| 4,526,168 | 6/1985 | Hassler et al. . |
| 4,617,931 | 10/1986 | Dory . |
| 4,620,546 | 11/1986 | Aida et al. . |
| 4,757,820 | 6/1988 | Itoh . |
| 4,798,215 | 1/1989 | Turner .................................. 607/102 |
| 5,065,740 | 11/1991 | Itoh ...................................... 128/24 EL |
| 5,065,741 | 11/1991 | Uchiyama et al. ................... 128/24 EL |
| 5,131,392 | 7/1992 | Jolesz et al. ......................... 128/653.2 |
| 5,166,875 | 11/1992 | Machida ................................... 324/309 |
| 5,178,146 | 1/1993 | Giese .................................... 128/653.2 |
| 5,201,311 | 4/1993 | Bottomley et al. .................. 128/653.2 |
| 5,207,214 | 5/1993 | Romano ............................... 128/24 EL |

FOREIGN PATENT DOCUMENTS

| | | |
|---|---|---|
| 0459535 | 12/1991 | European Pat. Off. . |
| 8713524 | 3/1989 | Germany . |
| 3913023 | 11/1989 | Germany . |
| WO91/11958 | 8/1991 | WIPO . |

OTHER PUBLICATIONS

Diagnostic Imaging, Sep. 1990, pp. 103–105; 108, Ferenc A. Jolesz, et al., "Laser Surgery Benefits from Guidance by MR".

*Primary Examiner*—Ruth S. Smith
*Attorney, Agent, or Firm*—Oblon, Spivak, McClelland, Maier & Neustadt

[57] ABSTRACT

An ultrasonic wave medical treatment in which the position of the focal point of the ultrasonic waves, the temperature in a vicinity of the object to be treated, and the effect of the treatment can be determined easily and accurately. The three-dimensional image information of the object to be treated obtained by a computed tomography device is utilized in locating the focal point. In case of using a nuclear magnetic resonance imaging device as the computed tomography device, the T2 weighted image and the chemical shift data can be used in checking the effect of the treatment and the temperature in a vicinity of the object. The endocavitary probe equipped with temperature and intensity sensors may also be used. The ultrasound tomographic images obtained by the ultrasound tomographic imaging device may also be used in conjunction with the three-dimensional image information. Sequential shifting of the focal point of the ultrasonic waves may be employed to reduce adverse influence due to the cavitation.

20 Claims, 8 Drawing Sheets

FIG. 13A    FIG. 13B
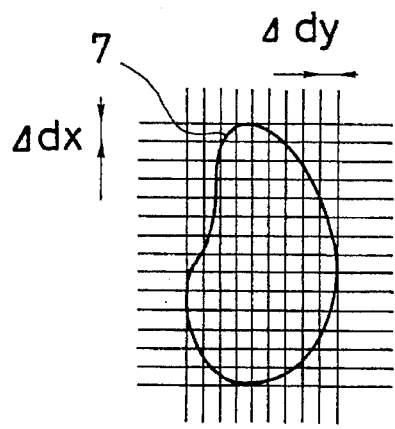 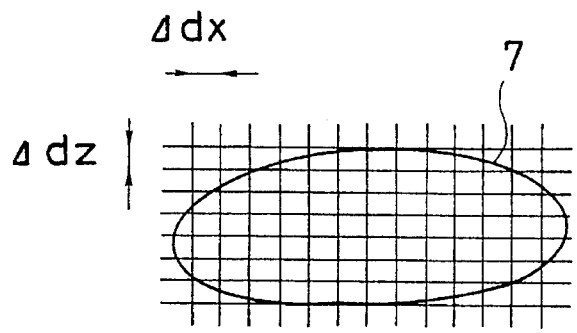
FIG. 14
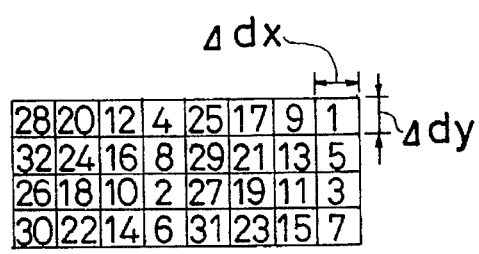

METHOD AND APPARATUS FOR ULTRASONIC WAVE MEDICAL TREATMENT USING COMPUTED TOMOGRAPHY

This application is a Continuation of application Ser. No. 08/022,911, filed on Feb. 26, 1993, now abandoned.

BACKGROUND OF THE INVENTION

1. Field of the Invention

The present invention relates to an ultrasonic wave medical treatment for treating treatment targets such as tumors, calculi, etc. inside a living body by applying ultrasonic waves thereon.

2. Description of the Background Art

In recent years, for a treatment of the calculosis, much attention has been attracted to a lithotriptor for destroying calculi inside a living body non-invasively by applying intense ultrasonic waves focused on the calculi to be destroyed in the living body.

For a source of the intense ultrasonic waves to be used in such a lithotriptor, there are many conventionally known sources including a source using a spark discharge in water, a source using an electromagnetic induction, a source using a small scale explosion, and a source using piezoelectric elements, each of which has its own advantages and disadvantages. Among them, the source using piezoelectric elements is known to have the disadvantage that the intensity of the ultrasonic waves at the focal point is rather small, but this type of source is also known to have several excellent advantages including the smallness of the size of the focal point, the elimination of the consumption, the controllability of the intense ultrasonic waves, the controllability of the position and the shape of the focal point by phase controlling the driving waveforms to be applied to a plurality of piezoelectric elements. (See, Japanese Patent Application Laid Open No. 60-145131. U.S. Pat. No. 4,526,168, and Japanese Patent Application Laid Open No. 62-42773.)

On the other hand, for a treatment of cancer, much attention has been attracted to a hyperthermia treatment which treats the cancer by utilizing the fact that the tumor tissues have higher thermal sensitivity than the normal tissues such that they can be killed by heating them at the temperature higher than 42.5° C. In such a hyperthermia, the localized heating of the tumor portion is known to be particularly effective.

For a heating method to be used in such a hyperthermia, the method utilizing the electromagnetic waves such as microwaves has been used conventionally. However, this conventional method of heating has a difficulty in selectively heating the tumor located deep inside the living body because of the electrical characteristics of the living body that affect the penetration of the electromagnetic waves, so that the satisfactory level of treatment has been realized only for the relatively superficial tumors located within 5 cm from the surface of the living body.

For this reason, for a treatment of the deeply located tumors, there has been a proposition to use a heating method utilizing the acoustic energy such as ultrasonic waves which utilizes the fact that the ultrasonic waves have superior focusing ability as well as deeper penetration range.

There is also a proposition for a treatment method in which the above described hyperthermia is further developed to burn the tumor tissues to death by heating the tumor portion at the temperature higher than 80° C., as disclosed in Japanese Patent Application No. 3-306106.

For a source of the ultrasonic waves to be used in such a hyperthermia using the ultrasonic waves, the conventionally proposed sources include an ultrasonic transducer constructed from a plurality of piezoelectric elements which has an overall spherical surface, and an annular array ultrasonic transducer constructed by arranging a plurality of ring shaped ultrasonic transducer elements concentrically. Among them, the annular array ultrasonic transducer has the advantage that the depth of the focal point can be varied electrically.

There is also a proposition for the phased array ultrasonic transducer in which the position of the focal point can be moved three-dimensionally, as disclosed in U.S. Pat. No. 4,526,168.

There is also a proposition for the treatment apparatus in which the above described lithotriptor is provided along the above described hyperthermia integrally, as disclosed in Japanese Patent Application No. 3-306106.

There is also a proposition for a hyperthermia treatment apparatus incorporating an ultrasonic wave source using piezoelectric elements in which the treatment target portion can be heated uniformly by utilizing the small focal point characteristic to the ultrasonic wave source using piezoelectric elements, as disclosed in Japanese Patent Application Laid Open No. 61-209643.

However, in this hyperthermia treatment apparatus, the focal point is moved continuously such that the ultrasonic waves are applied to neighboring regions sequentially. Consequently, it has been impossible in this hyperthermia treatment apparatus to carry out the treatment procedure including the application of the ultrasonic waves to two distanced points alternately or the avoidance of obstacles such as bones during the application of the ultrasonic waves, so that there is a danger of damaging the normal tissues in vicinities of the tumor tissues.

Moreover, in a case of applying the intense ultrasonic waves continuously at a fixed target position, the acoustic energy released immediately after the start of the application of the ultrasonic waves can reach to the target position without any obstruction, but the acoustic energy reaching to the target position will be gradually attenuated as air bubbles generated at or in vicinity of the focal point due to the cavitation caused by the intense ultrasonic waves themselves start to reflect the intense ultrasonic waves. The same problem due to the cavitation is also present in a case of applying the intense ultrasonic waves by moving the focal point slowly.

Here, the cavitation is the phenomenon in which the air bubbles (air cavities) are generated by tearing off the water through which the intense ultrasonic waves pass, as a very large tensile force is exerted to the water due to the influence of the negative pressure associated with the intense ultrasonic waves passing through the water. The air bubbles so generated will subsequently function as reflectors for the ultrasonic waves. Consequently, when a large amount of air bubbles generated by the cavitation are floating around the previous focal points to which the intense ultrasonic waves have already been applied, the acoustic energy of the intense ultrasonic waves applied to a new focal point in a vicinity of the previous focal points will be attenuated.

On the other hand, in a conventional hyperthermia treatment apparatus, the positioning of the focal point is achieved by utilizing the two-dimensional ultrasound tomographic images. However, the tumor to be treated very often has a complicated three-dimensional shape in practice, so that it has been very difficult to realize the complete treatment of the entire tumor by using the two-dimensional tomographic images.

To cope with this problem, there has been a proposition to utilize the three-dimensional ultrasound images, as disclosed in Japanese Patent Application Laid Open No. 61-209643.

However, in the ultrasound images, the region behind the bones and the pneumatic organs such as a lung becomes invisible, so that the full three-dimensional information cannot be provided, and only the relative position of the focal point and the treatment target portion can be ascertained at best.

Furthermore, such a conventional hyperthermia treatment apparatus has no means to judge the effect of the treatment made, so that whether to continue or discontinue the treatment cannot be decided over a considerably long period of time ranging from several weeks to several months required to ascertain the effect of the treatment by some conventionally known methods.

Moreover, it has been difficult in the conventional hyperthermia treatment apparatus to accurately determine the temperature at which the tumor portion is actually heated, so that it has been difficult to prevent the accidental overlooking of some tumor portions to be treated or the excessive heating of some portions to which the intense ultrasonic waves are applied.

SUMMARY OF THE INVENTION

It is, therefore, an object of the present invention to provide a method and an apparatus for an ultrasonic wave medical treatment capable of determining the position of the focal point of the ultrasonic waves easily and accurately.

It is another object of the present invention to provide a method and an apparatus for an ultrasonic wave medical treatment capable of determining the effect of the treatment easily and accurately, shortly after the treatment has actually been made.

It is another object of the present invention to provide a method and an apparatus for an ultrasonic wave medical treatment capable of determining the temperature in a vicinity of the object to be treated easily and accurately, such that the effective treatment of the tumor tissues can be realized without any potential for damaging the normal tissues around the tumor tissues.

According to one aspect of the present invention there is provided an ultrasonic medical treatment apparatus, comprising: ultrasonic wave applicator means for applying ultrasonic waves to an object to be treated; focal point control means for changing a focal point of the ultrasonic waves applied by the ultrasonic wave applicator means; computed tomography means for obtaining three-dimensional image information of the object to be treated; calculation means for determining a position of the focal point changed by the focal point control means in the three-dimensional image information obtained by the computed tomography means; and display means for displaying the three-dimensional image information obtained by the computed tomography means in superposition with the focal point at the position determined by the calculation means.

According to another aspect of the present invention there is provided a method of ultrasonic medical treatment, comprising the steps of: applying ultrasonic waves to an object to be treated with an ultrasonic wave applicator means; changing a focal point of the ultrasonic waves applied at the applying step; obtaining three-dimensional image information of the object to be treated by computed tomography means; determining a position of the focal point changed at the changing step in the three-dimensional image information obtained by the computed tomography means; and displaying the three-dimensional image information obtained by the computed tomography means in superposition with the focal point at the position determined at the determining step.

Other features and advantages of the present invention will become apparent from the following description taken in conjunction with the accompanying drawings.

BRIEF DESCRIPTION OF THE DRAWINGS

FIG. 13A and FIG. 13B are illustrations of division of a tumor into cells to be utilized in the application of the intense ultrasonic waves in the ultrasonic wave medical treatment apparatus of FIG. 10.

FIG. 14 is an illustration of the divided cells of a tumor for explaining an order of application of the intense ultrasonic waves in the ultrasonic wave medical treatment apparatus of FIG. 10.

DETAILED DESCRIPTION OF THE PREFERRED EMBODIMENTS

Figure 1:
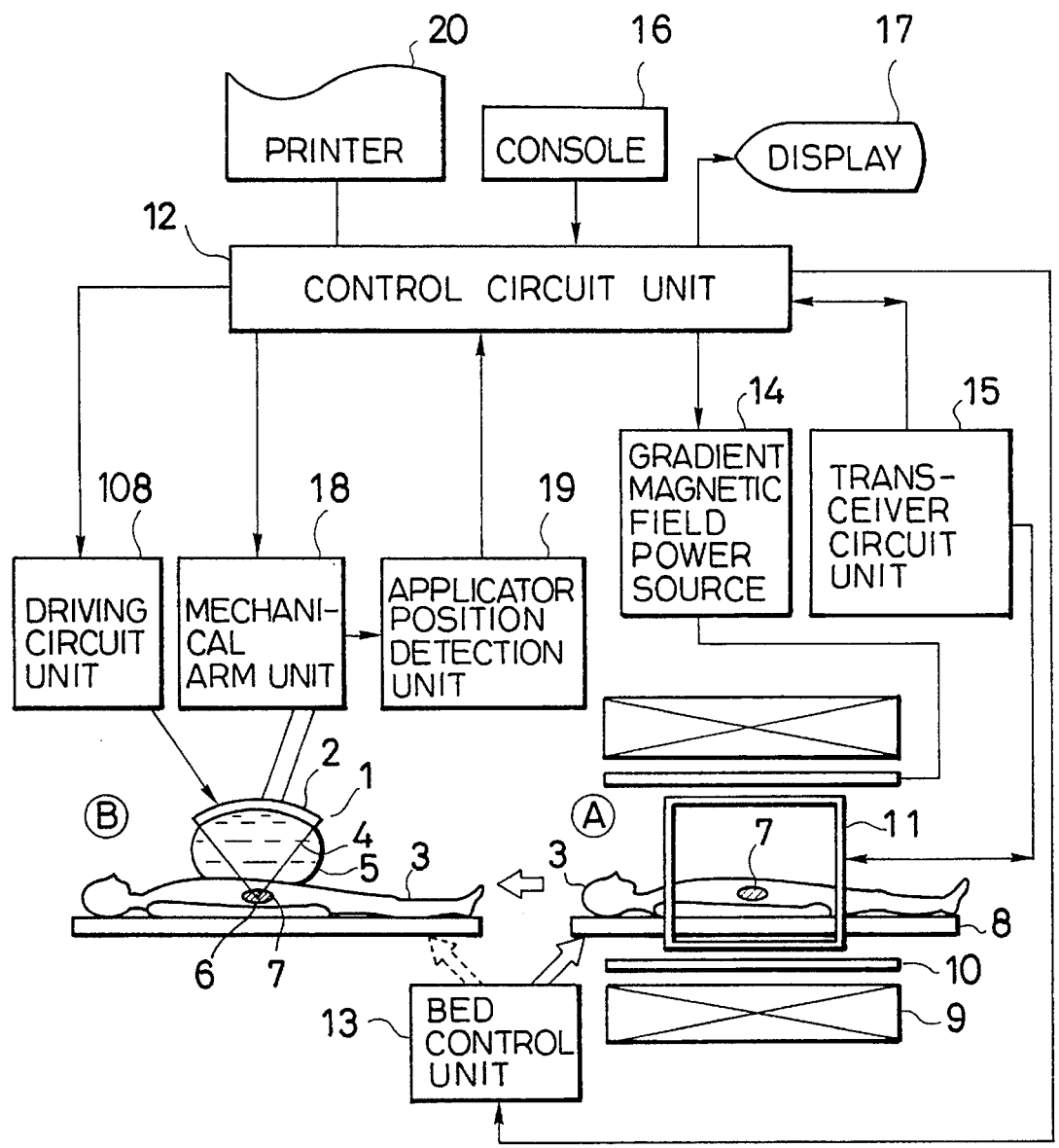
FIG. 1 is a schematic block diagram of a first embodiment of an ultrasonic wave medical treatment apparatus according to the present invention.

Referring now to FIG. 1, a first embodiment of an ultrasonic wave medical treatment apparatus according to the present invention will be described in detail.

In this first embodiment, the ultrasonic wave medical treatment apparatus generally comprises an ultrasonic wave treatment section, and a computed tomography (CT) section.

The ultrasonic wave treatment section includes: an ultrasonic wave applicator 1 constructed from an ultrasonic transducer 2 having a spherical surface for generating intense ultrasonic waves to be applied to a patient 3, an acoustic coupling fluid 4 for transmitting the intense ultrasonic waves generated by the ultrasonic transducer 2 to the patient 3, and a water bag 5 for containing the acoustic coupling fluid 4; a driving circuit unit 108 for driving the ultrasonic transducer 2 to generate the intense ultrasonic waves of a desired intensity; a mechanical arm unit 18 for controlling a position of the ultrasonic wave applicator 1 with respect to the patient 3; and an applicator position detection unit 19 for detecting a position of the ultrasonic wave applicator 1 controlled by the mechanical arm unit 18 by using potentiometers (not shown) attached on the mechanical arm unit 18.

In a case of applying the intense ultrasonic waves to the patient 3, the ultrasonic wave applicator 1 is placed on the body surface of the patient 3 with the water bag 5 facing toward the patient 3 such that the water bag 5 can make a contact with the body surface of the patient 3 through an ultrasonic jelly (not shown) provided thereon. Then, a focal point 6 of the intense ultrasonic waves to be generated by the ultrasonic transducer 2 is positioned to a tumor 7 to be treated inside the body of the patient 3. Then, the driving circuit unit 108 drives the ultrasonic transducer 2 so as to generate the intense ultrasonic waves of a desired intensity which are focused to the focal point 6 positioned at the tumor 7 such that the tumor 7 can be treated by being heated at a desired temperature.

On the other hand, in this first embodiment, the CT section comprises a nuclear magnetic resonance imaging (MRI) apparatus capable of obtaining usual nuclear magnetic resonance (NMR) tomographic images, which is constructed from a static magnetic field coil 9 with a central bore, an imaging gantry (not shown) inserted inside the central bore of the static magnetic field coil 9 which contains gradient magnetic field coils 10 and an RF coil 11 for transmitting RF pulses and receiving NMR signals, a gradient magnetic field power source 14 connected to the gradient magnetic field coils 10, and a transceiver circuit unit 15 connected to the RF coil 11.

In addition, the ultrasonic wave medical treatment apparatus of FIG. 1 further comprises: a bed 8 for placing the patient 3 lying thereon inside the imaging gantry while using the CT section and placing the patient 3 below the ultrasonic wave applicator 1 while using the ultrasonic wave treatment section; a bed control unit 13 for controlling a location of the bed 8; a control circuit unit 12 for controlling the operations of the driving circuit unit 108 and the mechanical arm unit 18 in the ultrasonic wave treatment section, the gradient magnetic field power source 14 and the transceiver circuit unit 15 in the CT section, and the bed control unit 13; an operator console 16 connected to the control circuit unit 12 for entering an ultrasonic wave treatment plan to be prepared by an operator (not shown); a CRT display 17 connected to the control circuit unit 12 for displaying various information to be utilized by the operator; and a printer 20 for printing various information to be utilized by the operator.

Now, the ultrasonic wave medical treatment apparatus of this first embodiment operates as follows.

First, the patient 3 is positioned on the bed 8 in a supine position, and carried inside the imaging gantry and set at a prescribed imaging position A by the bed 8 controlled by the bed control unit 13.

Then, the control circuit unit 12 controls the gradient magnetic field power source 14 and the transceiver circuit unit 15 according to the prescribed imaging sequence specified by the operator through the operator console 16 such that the usual multi-plane NMR tomographic images containing the tumor 7 to be treated can be obtained. The obtained NMR tomographic images are stored in a memory (not shown) provided in the control circuit unit 12.

Next, the control circuit unit 12 controls the CRT display 17 to display three-dimensional image information, constructed from the NMR tomographic images obtained by the CT section, as a static image in a suitable display format such as pseudo-three-dimensional display using wire frame.

At this point, the operator enters the ultrasonic wave treatment plan from the operator console 16 while viewing the three-dimensional image information containing the tumor 7 to be treated which is displayed on the CRT display 17. Here, the ultrasonic wave treatment plan specifies the scanning pattern for the focal point 6 and the desired intensity of the intense ultrasonic waves to be applied as well as the desired ultrasonic wave application timings and intervals and other parameters required to be specified in the ultrasonic wave treatment to be made by the ultrasonic wave treatment section. When the entering of the ultrasonic wave treatment plan is completed, the operator commands the start of the ultrasonic wave treatment from the operator console 16.

In response, the control circuit unit 12 controls the bed control unit 13 such that the bed 8 with the patient 3 lying thereon is moved to the ultrasonic wave treatment section and set to a prescribed treatment position B.

Then, the control circuit unit 12 controls the mechanical arm unit 18 such that the ultrasonic wave applicator 1 is placed on the patient 3 above the tumor 7 to be treated. During this positioning of the ultrasonic wave applicator 1, the control circuit unit 12 calculates the position of the focal point 6 of the intense ultrasonic waves to be applied according to the position of the ultrasonic wave applicator 1 detected by the applicator position detection unit 19 and a prescribed relationship between the position of the mechanical arm unit 18 and the imaging view field of the CT section, and controls the CRT display 17 to display the focal point 6 in superposition to the three-dimensional image information. In addition, the control circuit unit 12 may also calculate an incidence route of the intense ultrasonic waves such that the incidence route can also be displayed along with the focal point 6. This display of the incidence route of the intense ultrasonic waves can be useful in verifying the avoidance of obstacles in the ultrasonic wave treatment plan.

Then, after the ultrasonic wave applicator 1 is appropriately positioned on the patient 3 with the focal point 6 located at the tumor 7 to be treated as specified by the ultrasonic wave treatment plan, the control circuit unit 12 controls the driving circuit unit 108 to start the ultrasonic wave treatment.

In a middle and/or at an end of the ultrasonic wave treatment as specified by the ultrasonic wave treatment plan, the application of the intense ultrasonic waves are stopped, the ultrasonic wave applicator 1 is removed from the patient 3, and the bed 8 is moved back to the imaging position A in the CT section, in order to observe the progress and/or the effect of the ultrasonic wave treatment.

Here, the NMR tomographic images are taken again in the same manner as they were taken prior to the entering of the ultrasonic wave treatment plan, and then the NMR tomographic images taken before the ultrasonic wave treatment are compared with the NMR tomographic images taken after the ultrasonic wave treatment. For example, when the NMR tomographic images taken by the CT section are the T2 weighted images, the thermally degenerated region can be clearly visualized, so that it becomes possible for the operator to visually inspect the sufficiency of the treatment applied so far and to determine the need of the further treatment. Here, for the sake of easy visual comprehension, a difference image in which the NMR tomographic images taken after the ultrasonic wave treatment are subtracted from the NMR tomographic images taken before the ultrasonic wave treatment may be calculated by the control circuit unit 12 and displayed on the CRT display 17.

It is to be noted that any desired number of such inspections using the NMR tomographic image taking may be incorporated into the ultrasonic wave treatment plan in advance such that the NMR tomographic image taking can be made automatically at specified timings. In addition, it is also possible to automatically determine an untreated region of the tumor 7 which is not yet thermally degenerated and should be subjected to the further treatment by comparing the NMR tomographic images taken before and after the ultrasonic wave treatment, and the focal point 6 of the intense ultrasonic waves to be applied by the ultrasonic wave applicator 1 for the further treatment can be automatically set to the determined untreated region.

It is also to be noted that by taking the NMR chemical shift data before and after the ultrasonic wave treatment, it also becomes possible to determine the change of the temperature at various parts within the body of the patient 3, so that the occurrence of the excessive heating can also be visually inspected by the operator. Here, again, for the sake of easy visual comprehension, a difference image in which the chemical shift data taken after the ultrasonic wave treatment are subtracted from the chemical shift data taken before the ultrasonic wave treatment may be calculated by the control circuit unit 12 and displayed on the CRT display 17.

When the effect of the ultrasonic wave treatment is judged to be sufficient by the operator according to the above described visual inspection, the operator commands the end of the ultrasonic wave treatment from the operator console 16. At this point, the record of the ultrasonic wave treatment conducted may be outputted either on the CRT display 17 or from the printer 20.

Thus, according to this first embodiment, it becomes possible to realize an ultrasonic wave medical treatment apparatus capable of determining the position of the focal point of the ultrasonic waves easily and accurately, as the focal point can be displayed along with the three-dimensional image information constructed from the NMR tomographic images obtained by the CT section.

In addition, it also becomes possible in this first embodiment to realize an ultrasonic wave medical treatment apparatus capable of determining the effect of the treatment, shortly after the treatment has actually been made, by taking and comparing the suitable NMR tomographic images before and after the ultrasonic wave treatment.

Furthermore, it also becomes possible in this first embodiment to realize an ultrasonic wave medical treatment apparatus capable of determining the temperature in a vicinity of the treatment target portion accurately, by taking the chemical shift data, such that the effective treatment of the tumor tissues can be realized without any potential for damaging the normal tissues.

It should be obvious that the CT section of the ultrasonic wave medical treatment apparatus of the first embodiment described above may comprise a tomographic imaging apparatus other than the MRI apparatus, such as an X-ray CT apparatus.

It should also be obvious that the ultrasonic wave medical treatment apparatus of the first embodiment described above is equally applicable for the ultrasonic wave medical treatment other than the hyperthermia such as the lithotriptor.

Figure 2:
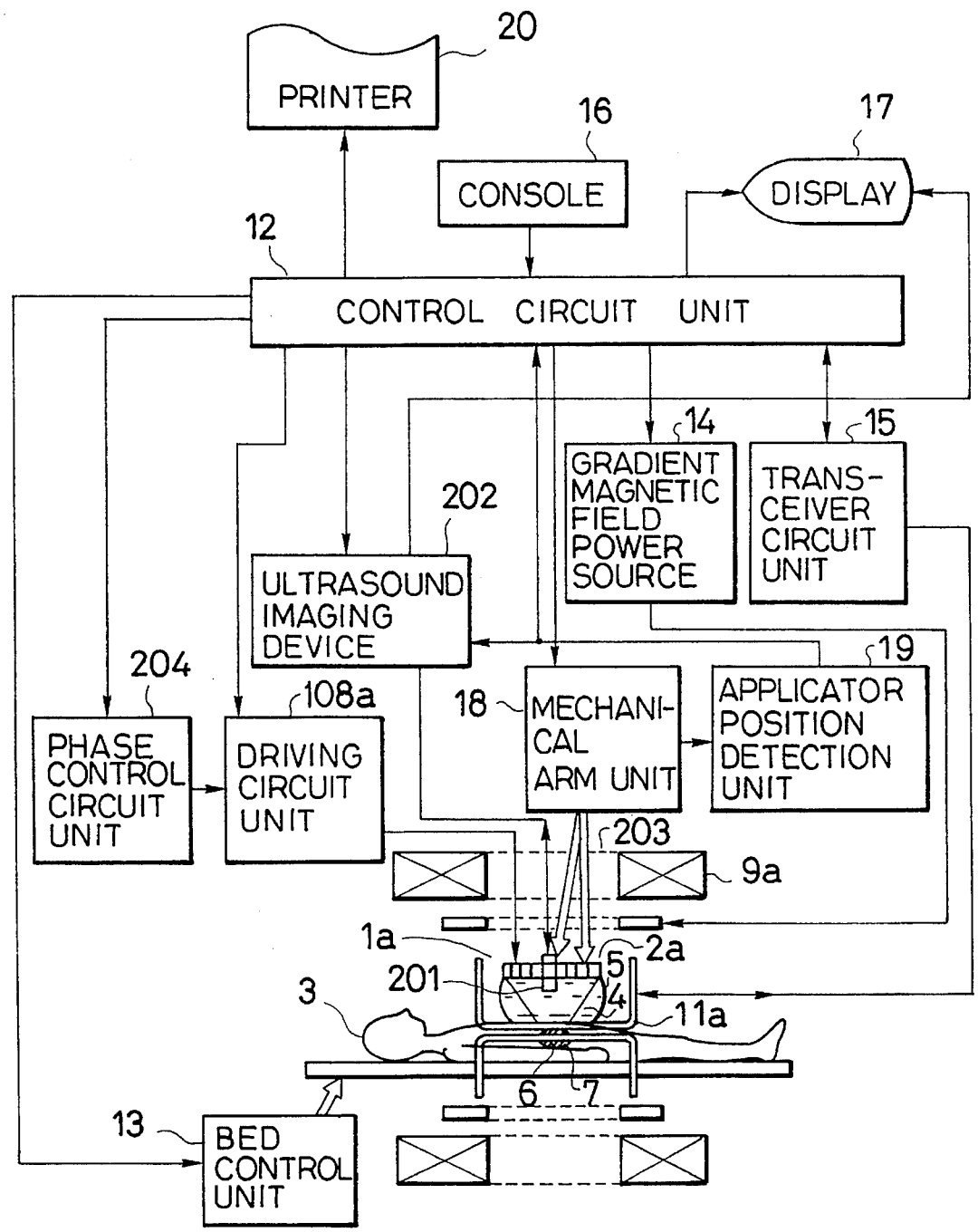
FIG. 2 is a schematic block diagram of a second embodiment of an ultrasonic wave medical treatment apparatus according to the present invention.

Referring now to FIG. 2, a second embodiment of an ultrasonic wave medical treatment apparatus according to the present invention will be described in detail. Here, those elements which are substantially equivalent to the corresponding elements in the first embodiment described above will be given the same reference numerals and their description will be omitted, while those elements which are incorporating significant modifications over the corresponding elements in the first embodiment described above will be given the same reference numerals of the corresponding elements accompanied by the suffix "a".

Figure 3:
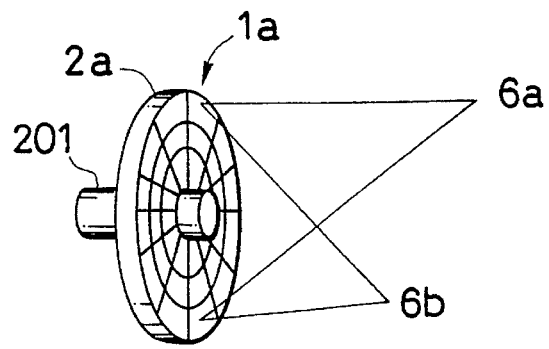
FIG. 3 is a perspective view of a phased array ultrasonic transducer to be used in the ultrasonic wave medical treatment apparatus shown in FIG. 2.

In this second embodiment, in the ultrasonic wave treatment section, the source of the intense ultrasonic waves to be applied is provided in a form of a phased array ultrasonic wave applicator 1a. Here, the phased array ultrasonic wave applicator 1a is constructed in a form shown in FIG. 3 in which a planar disk shaped ultrasonic transducer 2a is divided in radial and circumferential directions to realize a plurality of mutually independent phased array channels.

This phased array ultrasonic wave applicator 1a is also equipped with an ultrasonic wave probe 201 for collecting ultrasound imaging data to be used in the ultrasound tomographic imaging to be made by an ultrasound imaging device 202, where the ultrasonic wave probe 201 is located at a center of the planar disk shaped ultrasonic transducer 2a to be rotatable around its central axis as well as to be movable along its central axis.

The driving circuit unit 108a to drive this phased array ultrasonic wave applicator 1a is formed from a group of driving circuits in correspondence to the divided phased array channels of the planar disk shaped ultrasonic transducer 2a of the phased array ultrasonic wave applicator 1a, and there is also provided a phase control circuit unit 204 which provides mutually independent timing signals for controlling the driving circuits of the driving circuit unit 108a independently from each other, where the timing signals are appropriately delayed by the phase control circuit unit 204 according to the control from the control circuit unit 12 in order to realize a desired phase distribution among the phased array channels. By adjusting the phase distribution among the phased array channels appropriately, the focal point of the intense ultrasonic waves to be generated by the phased array ultrasonic wave applicator 1a can be set to an arbitrary position in three-dimensional space, as indicated by the focal points 6a and 6b in FIG. 3 for example. The further detail of the phased array ultrasonic wave applicator 1a can be found in U.S. Pat. No. 4,526,168.

In this second embodiment, the applicator position detection unit 19 not only detects the position of the phased array ultrasonic wave applicator 1a as a whole, but also a relative position of the ultrasonic wave probe 201 with respect to the imaging view field of the CT section, and supplies this information to the control circuit unit 12 as well as to the ultrasound imaging device 202.

The ultrasound imaging device 202 is connected directly to the CRT display 17 and also receives the information on the position of the focal point 6 set up by the phased array ultrasonic wave applicator 1a from the control circuit unit 12, such that the ultrasound tomographic images of the tumor 7 to be treated obtained by the ultrasound imaging device 202 can be displayed on the CRT display 17 during the ultrasonic wave treatment in real time, along with the position of the focal point 6 of the intense ultrasonic waves applied.

Figure 4:
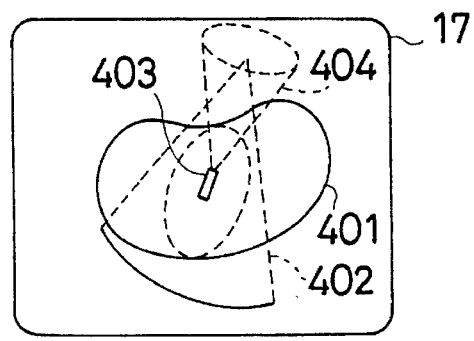
FIG. 4 is an illustration of an exemplary display to be used in the ultrasonic wave medical treatment apparatus shown in FIG. 2.

The CRT display 17 is also capable of displaying the display image as shown in FIG. 4 in which the static three-dimensional image information 401 constructed from the NMR tomographic images obtained by the CT section prior to the attaching of the phased array ultrasonic wave applicator 1a to the patient 3 is shown along with the slice plane 402 currently scanned by the ultrasonic wave probe 201, the focused region 403 and the incidence route 404 of the intense ultrasonic waves applied.

On the other hand, in this second embodiment, the static magnetic field coil 9a and the gradient magnetic field coils 10a of the CT section comprising the MRI apparatus are formed in the Helmholtz type with a central bore region 203 along a vertical direction, while the phased array ultrasonic wave applicator 1a is formed from non-magnetic materials, so that it becomes possible to attach the phased array ultrasonic wave applicator 1a to the patient 3 through this central bore region 203 by simply changing the orientation of the RF coil 11, without moving the patient 3. Consequently, there is no need to change the position of the patient 3 in the NMR tomographic image taking procedure and the ultrasonic wave treatment procedure, such that the timing difference between the ultrasonic wave treatment and the visual inspection using the NMR tomographic image taking can be reduced and the potentially troublesome influence of the body movement by the patient 3 during the period between these two operations can also be reduced.

Thus, according to this second embodiment, it becomes possible to realize an ultrasonic wave medical treatment apparatus capable of determining the position of the focal point of the ultrasonic waves easily and accurately, just as in the first embodiment described above, as the focal point can be displayed along with the three-dimensional image information constructed from the NMR tomographic images.

In addition, it also becomes possible in this second embodiment to realize an ultrasonic wave medical treatment apparatus capable of determining the effect of the treatment, shortly after the treatment has actually been made, by taking and comparing the suitable NMR tomographic images before and after the ultrasonic wave treatment, which can be done more quickly and accurately than the first embodiment as there is no need to move the patient between the ultrasonic wave treatment section and the CT section.

Furthermore, it also becomes possible in this second embodiment to realize an ultrasonic wave medical treatment apparatus capable of determining the temperature in a vicinity of the treatment target portion accurately, by taking the chemical shift data, such that the effective treatment of the tumor tissues can be realized without any potential for damaging the normal tissues, just as in the first embodiment described above.

Figure 5:
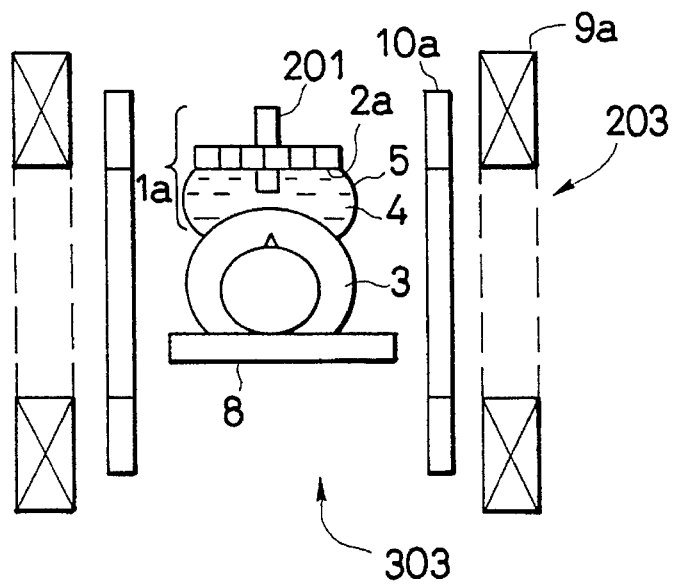
FIG. 5 is a schematic diagram of an alternative spatial arrangement of a static magnetic field coil and gradient magnetic field coils in a CT section of the ultrasonic wave medical treatment apparatus of FIG. 2.

It is to be noted here that the spatial arrangement of the static magnetic field coil 9a and the gradient magnetic field coils 10a in the Helmholtz type as shown in FIG. 2 may be replaced by an alternative spatial arrangement shown in FIG. 5 in which the central bore region 203 is provided along a horizontal direction. In this case, the phased array ultrasonic wave applicator 1a can be attached to the patient 3 through a side opening 303 between the coil pairs of the static magnetic field coil 9a and the gradient magnetic field coils 10a. Also, in this case, although not depicted in FIG. 5, the spatial arrangement of the RF coil 11a must be changed in accordance with the change of the directions of the static and gradient magnetic fields produced by the static magnetic field coil 9a and the gradient magnetic field coils 10a.

It is also to be noted that the phased array ultrasonic wave applicator 1a may be replaced by the annular array ultrasonic wave applicator.

It should be obvious that the CT section of the ultrasonic wave medical treatment apparatus of the second embodiment described above may comprise a tomographic imaging apparatus other than the MRI apparatus, such as an X-ray CT apparatus.

It should also be obvious that the ultrasonic wave medical treatment apparatus of the second embodiment described above is equally applicable for the ultrasonic wave medical treatment other than the hyperthermia such as the lithotriptor.

Figure 6:
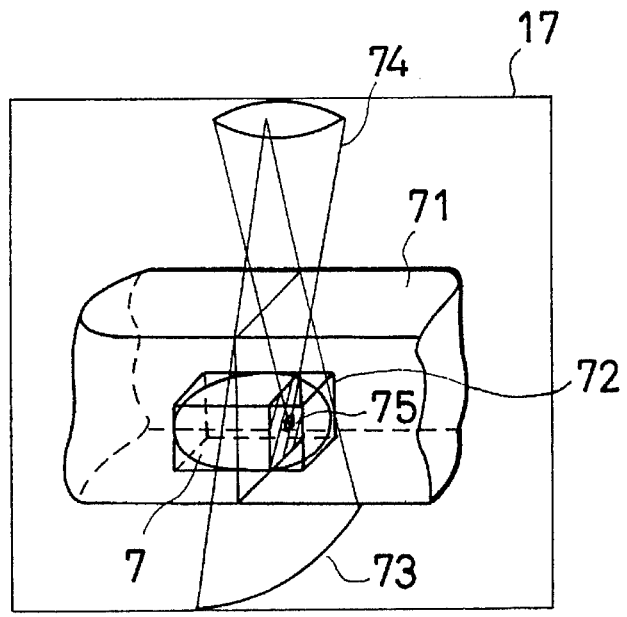
FIG. 6 is an illustration of an exemplary display to be used in a third embodiment of the ultrasonic wave medical treatment apparatus according to the present invention, at a time of entering the ultrasonic wave treatment plan.
Figure 7:
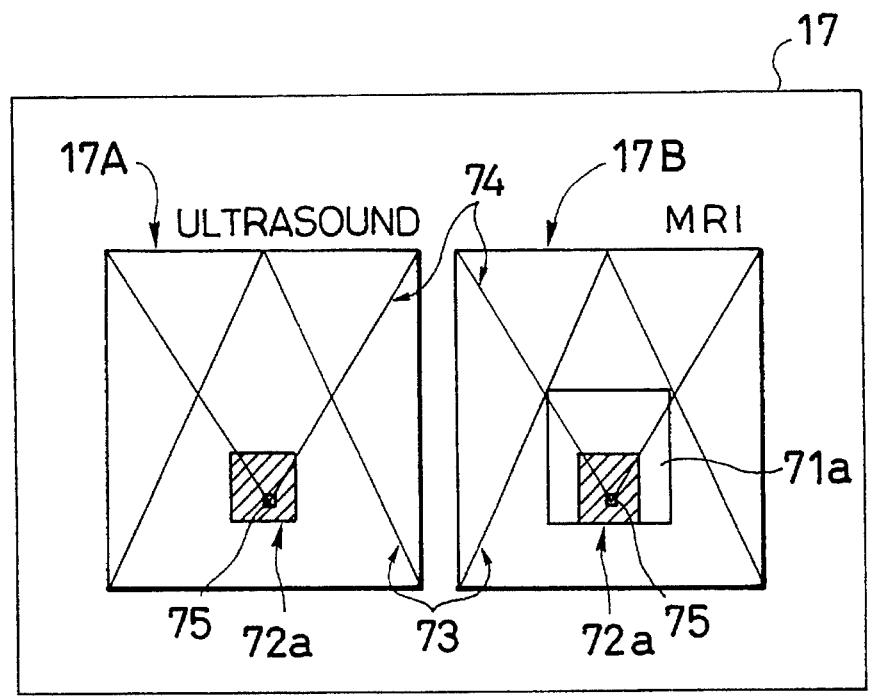
FIG. 7 is an illustration of an exemplary display to be used in a third embodiment of the ultrasonic wave medical treatment apparatus according to the present invention, at a time of executing the ultrasonic wave treatment.

Referring now to FIG. 6 and FIG. 7, a third embodiment of an ultrasonic wave medical treatment apparatus according to the present invention will be described in detail. Here, those elements which are substantially equivalent to the corresponding elements in the second embodiment described above will be given the same reference numerals and their description will be omitted.

In this third embodiment, the ultrasonic wave medical treatment apparatus having a configuration substantially identical to that shown in FIG. 2 described above for the second embodiment is used.

This third embodiment differs from the second embodiment described above in that, in addition to the three-dimensional image information, the CT section also provides two-dimensional tomographic image information corresponding to the two-dimensional ultrasound tomographic images taken by the ultrasound imaging device 202.

More specifically, in this third embodiment, the ultrasonic wave medical treatment apparatus of FIG. 2 operates as follows.

First, the patient 3 is positioned on the bed 8 in a supine position, and carried inside the imaging gantry by the bed 8 controlled by the bed control unit 13.

Then, the control circuit unit 12 controls the gradient magnetic field power source 14 and the transceiver circuit unit 15 according to the prescribed imaging sequence specified by the operator through the operator console 16 such that the usual multi-plane NMR tomographic images containing the tumor 7 to be treated can be obtained. The obtained NMR tomographic images are stored in a memory (not shown) provided in the control circuit unit 12.

Next, the control circuit unit 12 controls the CRT display 17 to display three-dimensional image information constructed from the NMR tomographic images obtained by the CT section in a form of a static MRI image 71 including the image of the tumor 7 to be treated as shown in FIG. 6, presented in a suitable display format such as pseudo-three-dimensional display using wire frame. Here, the CRT display 17 displays the static MRI image 71 along with the scanning region 72 of the focal point 6 of the intense ultrasonic waves applied, the slice plane 73 currently scanned by the ultrasonic wave probe 201, and the incidence route 74 and the currently focused region 75 of the intense ultrasonic waves applied, in order to assist the operator to properly planning the avoidance of obstacles in the ultrasonic wave treatment plan.

At this point, the operator enters the ultrasonic wave treatment plan From the operator console 16 while viewing the three-dimensional image information containing the tumor 7 to be treated which is displayed on the CRT display 17. Here, the ultrasonic wave treatment plan specifies the scanning pattern for the focal point 6 and the desired intensity of the intense ultrasonic waves to be applied as well as the desired ultrasonic wave application timings and intervals and other parameters required to be specified in the ultrasonic wave treatment to be made by the ultrasonic wave treatment section.

When the entering of the ultrasonic wave treatment plan is completed, the operator commands the start of the ultrasonic wave treatment from the operator console 16.

In response, the control circuit unit 12 controls the mechanical arm unit 18 such that the ultrasonic wave applicator 1 is placed on the patient 3 above the tumor 7 to be treated.

Then, after the ultrasonic wave applicator 1 is appropriately positioned on the patient 3 with the focal point 6 located at the tumor 7 to be treated as specified by the ultrasonic wave treatment plan, the control circuit unit 12 controls the driving circuit unit 108a to start the ultrasonic wave treatment.

Here, as shown in FIG. 7, during the ultrasonic wave treatment, the CRT display 17 displays the ultrasound tomographic image 17A obtained by the ultrasound imaging device 202 in real time, along with the corresponding MRI tomographic image 17B of the same slice plane and view field as the ultrasound tomographic image 17A, where the MRI tomographic image 17B contains the reconstructed two-dimensional tomographic image 71a obtained by the CT section prior to the attaching of the phased array ultrasonic wave applicator 1a to the patient 3, in order to assist the operator's comprehension of the currently treated region shown on the ultrasound tomographic image 17A. Namely, by comparing the ultrasound tomographic image 17A with the simultaneously displayed MRI tomographic image 17B that has been used in making the ultrasonic wave treatment plan, it becomes easier for the operator to comprehend the displayed content of the ultrasound tomographic image 17A. Here, for the sake of the better comprehension, these ultrasound tomographic image 17A and the MRI tomographic image 17B are also displayed along with the scanning area 72a for the focal point 6 of the intense ultrasonic waves applied, the slice plane 73 currently scanned by the ultrasonic wave probe 201, and the incidence route 74 and the currently focused region 75 of the intense ultrasonic waves applied.

In this display by the CRT display 17, the change of the slice plane and the view field in the ultrasound tomographic image 17A due to the movement of the ultrasonic wave probe 201 is closely followed by the reconstructed two-dimensional tomographic image 71a by utilizing the obtained NMR tomographic images stored in the aforementioned memory provided in the control circuit unit 12. Therefore, when any discrepancy between the ultrasound tomographic image 17A and the MRI tomographic image 17B is found, the discrepancy can be attributed to the body movement by the patient 3, so that the re-positioning of the patient 3 can be made immediately.

In addition, during the ultrasonic wave treatment, the CRT display 17 displays those regions to which the intense ultrasonic waves have been applied in color, in order to facilitate an easy and accurate comprehension of the progress of the ultrasonic wave treatment. The coloring scheme other than this may also be incorporated on either one or both of the ultrasound tomographic image 17A and the MRI tomographic image 17B.

It is also possible to display the MRI tomographic image 17B in the extended or contracted scale different from the size of the ultrasound tomographic image 17A. It is also possible to display the display as shown in FIG. 7 along with the display as shown in FIG. 6 simultaneously.

The ultrasonic wave treatment is carried out automatically under the control by the control circuit unit 12 according to the ultrasonic wave treatment plan entered by the operator, but the manual control by the operator may also be provided. In a case of the manual control, the deviation from the entered ultrasonic wave treatment plan can be notified to the operator by using either one or both of the alarm sound and display message. Here, however, the operator should be able to revise the ultrasonic wave treatment plan stored in the control circuit unit 12 from the operator console 16 during the ultrasonic wave treatment, if necessary.

Similarly to the first embodiment described above, in a middle and/or at an end of the ultrasonic wave treatment as specified by the ultrasonic wave treatment plan, the application of the intense ultrasonic waves is stopped and the ultrasonic wave applicator 1 is removed from the patient 3, in order to observe the progress and/or the effect of the ultrasonic wave treatment.

Here, the NMR tomographic images are taken again in the same manner as they were taken prior to the entering of the ultrasonic wave treatment plan, and then the NMR tomographic images taken before the ultrasonic wave treatment are compared with the NMR tomographic images taken after the ultrasonic wave treatment. For example, when the NMR tomographic images taken by the CT section are the T2 weighted images, the thermally degenerated region can be clearly visualized, so that it becomes possible for the operator to visually inspect the sufficiency of the treatment applied so far and to determine the need of the further treatment. Here, for the sake of easy vidual comprehension, a difference image in which the NMR tomographic images taken after the ultrasonic wave treatment are subtracted from the NMR tomographic images taken before the ultrasonic wave treatment may be calculated by the control circuit unit 12 and displayed on the CRT display 17.

It is to be noted that any desired number of such inspections using the NMR tomographic image taking may be incorporated into the ultrasonic wave treatment plan in advance such that the NMR tomographic image taking can be made automatically at specified timings. In addition, it is also possible to automatically determine an untreated region of the tumor 7 which is not yet thermally degenerated and should be subjected to the further treatment by comparing the NMR tomographic images taken before and after the ultrasonic wave treatment, and the focal point 6 of the intense ultrasonic waves to be applied by the ultrasonic wave applicator 1 for the further treatment can be automatically set to the determined untreated region.

It is also to be noted that by taking the NMR chemical shift data before and after the ultrasonic wave treatment, it also becomes possible to determine the change of the temperature at various parts within the body of the patient 3, so that the occurrence of the excessive heating can also be visually inspected by the operator. Here, again, for the sake of easy vidual comprehension, a difference image in which the chemical shift data taken after the ultrasonic wave treatment are subtracted from the chemical shift data taken before the ultrasonic wave treatment may be calculated by the control circuit unit 12 and displayed on the CRT display 17.

When the effect of the ultrasonic wave treatment is judged to be sufficient by the operator according to the above described visual inspection, the operator commands the end of the ultrasonic wave treatment from the operator console 16. At this point, the record of the ultrasonic wave treatment conducted may be outputted either on the CRT display 17 or from the printer 20.

Also, similarly to the second embodiment described above, the static magnetic field coil 9a and the gradient magnetic field coils 10a of the CT section comprising the MRI apparatus are formed in the Helmholtz type with the central bore region 203 while the phased array ultrasonic wave applicator 1a is formed from non-magnetic materials, so that it becomes possible to attach the phased array ultrasonic wave applicator 1a to the patient 3 through this central bore region 203 by simply changing the orientation of the RF coil 11, without moving the patient 3. Consequently, there is no need to change the position of the patient 3 in the NMR tomographic image taking procedure and the ultrasonic wave treatment procedure, such that the timing difference between the ultrasonic wave treatment and the visual inspection using the NMR tomographic image taking can be reduced and the potentially troublesome influence of the body movement by the patient 3 during the period between these two operations can also be reduced.

Thus, according to this third embodiment, in addition to the advantages of the second embodiment described above, it becomes possible to assist the operator's comprehension of the real time display of the ultrasound tomographic images during the ultrasonic wave treatment by also displaying the static image of the corresponding two-dimensional tomographic image obtained at the CT section, such that the accuracy and the efficiency in the ultrasonic wave treatment can be improved.

Figure 8:
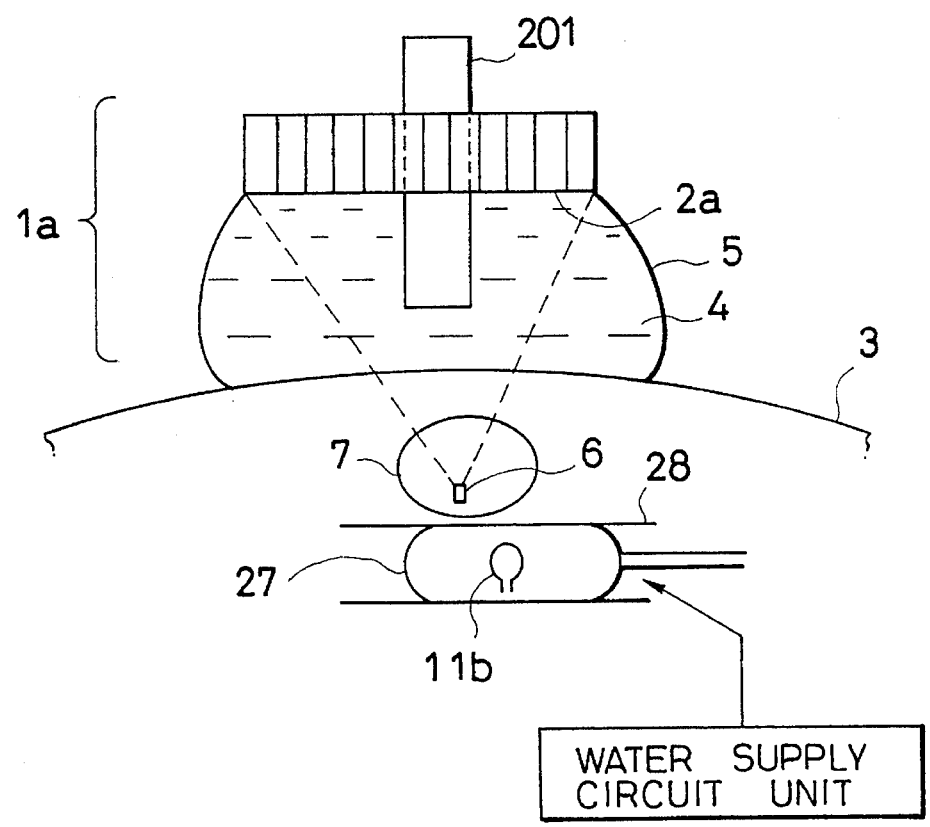
FIG. 8 is a diagrammatic illustration of positioning of a phased array ultrasonic wave transducer and an endocavitary probe to be used in a fourth embodiment of the ultrasonic wave medical treatment apparatus according to the present invention.
Figure 9:
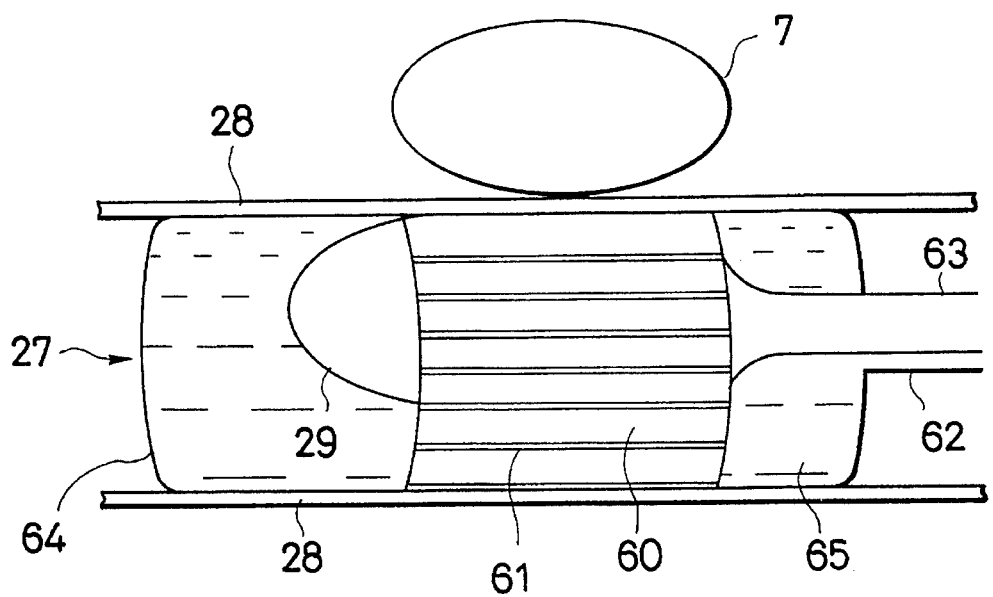
FIG. 9 is an enlarged view of the endocavitary probe shown in FIG. 8 to be used in a fourth embodiment of the ultrasonic wave medical treatment apparatus according to the present invention.

Referring now to FIG. 8 and FIG. 9, a fourth embodiment of an ultrasonic wave medical treatment apparatus according to the present invention will be described in detail. Here, those elements which are substantially equivalent to the corresponding elements in the second embodiment described above will be given the same reference numerals and their description will be omitted.

In this fourth embodiment, the ultrasonic wave medical treatment apparatus to be used has a configuration substantially identical to that shown in FIG. 2 described above for the second embodiment, except that the RF coil 11a used in the configuration of FIG. 2 is replaced by an endocavitary RF coil 11b provided inside an endocavitary probe 27 to be inserted into a body cavity of the patient 3 as shown in FIG. 8.

The endocavitary probe 27 has a configuration as shown in FIG. 9, which shows a case in which the endocavitary prove 27 is inserted into the rectum in order to treat tumor 7 of the prostate cancer located nearby an intestinal wall 28 of the rectum. As shown in FIG. 9, the endocavitary probe 27 comprises: a probe body 29 containing the endocavitary RF coil 11b therein; an elastic water bag 64 surrounding the probe body 29 to be filled with water 65 to be supplied from an externally located water supply circuit unit 66; a plurality of temperature sensors 60 such as thermo-couples and intensity sensors 61 such as PVDF films which are provided around the water bag 64 for measuring the temperature at the positions of the temperature sensors 60 and the intensity of the intense ultrasonic waves at the positions of the intensity sensors 61, respectively; a water supply hose 62 for supplying the water 65 to fill the water bag 64 from the water supply circuit unit 66; and a cable 63 for transmitting the information collected by the endocavitary probe 27 as well as the signals to be supplied to the endocavitary probe 27.

This endocavitary probe 27 is inserted into the rectum of the patient 3 to a position in a vicinity of the tumor 7 to be treated through which the intense ultrasonic waves to be applied in the ultrasonic wave treatment will pass. Then, the water 65 is filled into the water bag 64 from the water supply circuit unit 66, such that there is no air in the incidence route of the intense ultrasonic waves to be applied. This removal of air from the incidence route of the intense ultrasonic waves has the effect of preventing the damaging of the nearby normal tissues due to the tensile force that can be caused by the reflection of the intense ultrasonic waves at the boundary of the air and the living body.

Here, the temperature sensors 60 and the intensity sensors 61 are provided on the surface of the water bag 64 such that they will not make any contact with the water 65 filled in the water bag 64, and they make direct contacts with the intestinal wall 28. In addition, a plurality of temperature sensors 60 and intensity sensors 61 are arranged at regular interval around the entire circumference of the water bag 64 as shown in FIG. 9, so that there is no need to rotate the endocavitary probe 27 after the endocavitary probe 27 is inserted into the rectum in order to bring the temperature sensors 60 and the intensity sensors 61 in contact with the intestinal wall 28.

The NMR tomographic image taking operation by the CT section is carried out with the endocavitary probe 27 at this position in this fourth embodiment, because the endocavitary RF coil 11b can be located very close to the source of the NMR signals, the NMR tomographic images of high image quality can be obtained in this NMR tomographic image taking operation.

Then, in executing the ultrasonic wave treatment, the endocavitary probe 27 is left at this position, such that when the intense ultrasonic waves are applied from the phased array ultrasonic wave applicator 1a, the temperature sensors 60 and the intensity sensors 61 measure the temperature at the positions of the temperature sensors 60 and the intensity of the intense ultrasonic waves at the positions of the intensity sensors 61, respectively, and these data are transmitted through the cable 63 to the control circuit unit 12. In response, the control circuit unit 12 calculates the differences between the prescribed optimal values for the temperature and the intensity with the maximum values of the temperatures and the intensities measured by the temperature sensors 60 and the intensity sensors 61, and adjust the controlling of the phase control circuit unit 204 to minimize the calculated differences.

Throughout these operations, the water 65 filling the water bag 64 is circulated by the control from the water supply circuit unit 66 such that the water 65 functions as coolant for preventing the potential damage of the intestinal wall 28 by the excessive heating.

It is to be noted that the similar operations can be carried out for the tumors at the organs other than the prostate, such as bladder and uterine.

It is also to be noted that the endocavitary probe 27 described above may be adapted by the configuration of FIG. 1 for the first embodiment described above, instead of the configuration of FIG. 2 as described.

Thus, according to this fourth embodiment, in addition to the advantages of the second embodiment described above, it becomes possible to utilize the information concerning the temperature and the intensity of the intense ultrasonic waves applied at the position of the endocavitary probe during the ultrasonic wave treatment, so that the accuracy and the efficiency in the ultrasonic wave treatment can be improved.

Figure 10:
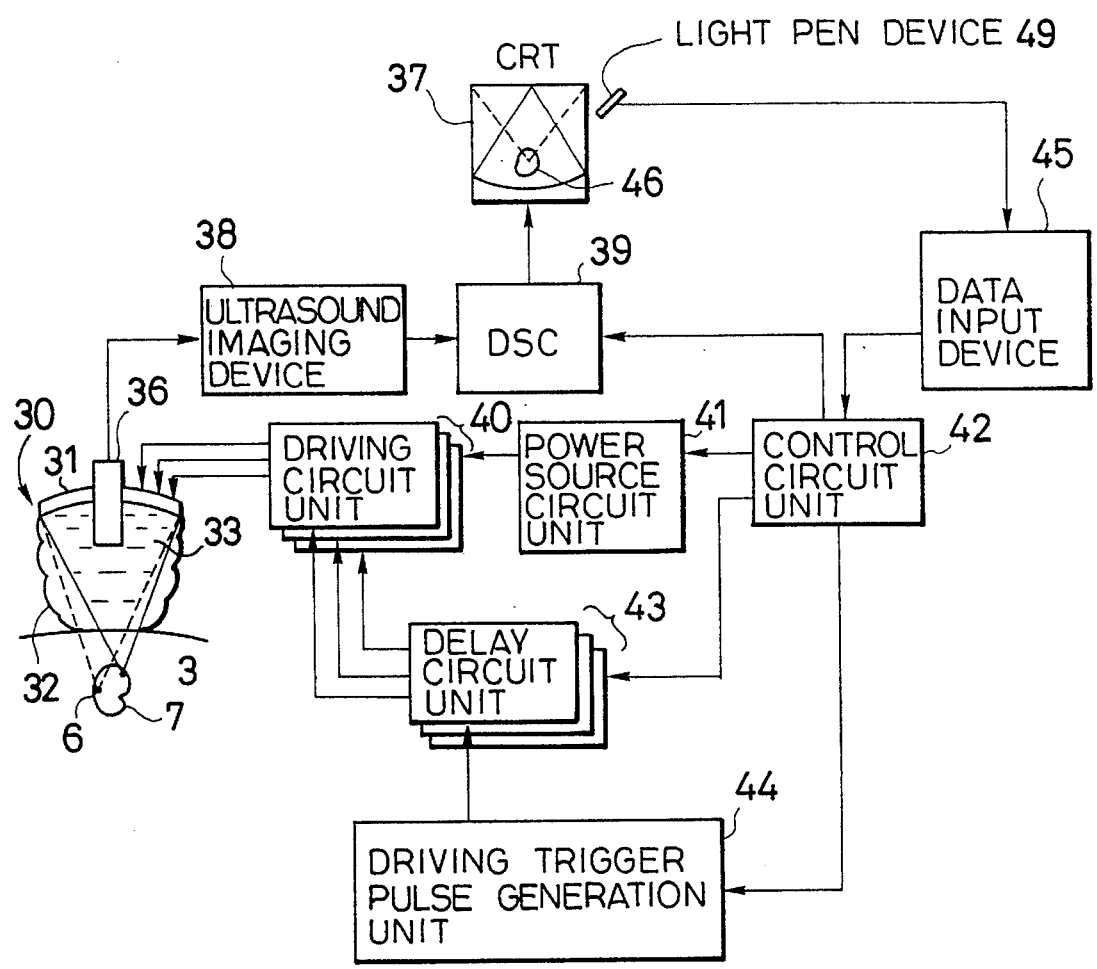
FIG. 10 is a schematic block diagram of a main part of a fifth embodiment of an ultrasonic wave medical treatment apparatus according to the present invention.

Referring now to FIG. 10, a fifth embodiment of an ultrasonic wave medical treatment apparatus according to the present invention will be described in detail.

In this fifth embodiment, the ultrasonic wave medical treatment apparatus generally comprises an ultrasonic wave treatment section, and a computed tomography (CT) section as in the first to fourth embodiments described above, where the CT section has a configuration substantially similar to that used in either one of the first or second embodiment described above, so that its description will be omitted.

The ultrasonic wave treatment section of this fifth embodiment has a configuration as shown in FIG. 10, which includes a phased array ultrasonic wave applicator 30 constructed from an ultrasonic transducer 31 having a spherical surface for generating intense ultrasonic waves to be applied to the tumor 7 in the patient 3 which is formed by a plurality of piezoelectric elements, an acoustic coupling fluid 33 for transmitting the intense ultrasonic waves generated by the ultrasonic transducer 31 to the patient 3, a water bag 32 for containing the acoustic coupling fluid 33, and an ultrasonic wave probe 36 for collecting ultrasound imaging data which is located at a center of the ultrasonic transducer 32 to be rotatable around its central axis as well as to be movable along its central axis.

The ultrasonic wave treatment section of FIG. 10 further includes: a driving circuit unit 40 containing a plurality of driving circuits for driving a plurality of phased array channels of the ultrasonic transducer 31 to generate the intense ultrasonic waves of a desired intensity; a power source circuit unit 41 for supplying a driving power to the driving circuit unit 40; a delay circuit unit 43 containing a plurality of delay circuits for controlling driving timings of a plurality of driving circuits in the driving control circuit unit 40; a driving trigger pulse generation unit 44 for generating a driving trigger pulse to be supplied to the delay circuit unit 43; and a control circuit unit 42 for controlling the operations of the power source circuit unit 41, the delay circuit unit 43, and the driving trigger pulse generation unit 44.

Here, the focal point 6 of the intense ultrasonic waves to be applied from the phased array ultrasonic wave applicator 80 can be changed by controlling the driving timings of a plurality of driving circuits in the driving control circuit unit 40 from the delay circuit unit 43 under the appropriate control by the control circuit unit 42. In a case of heating the tumor 7 to be treated, the driving circuit unit 40 is controlled to supply the bursty signals of a constant voltage level to the phased array ultrasonic wave applicator 30 continuously. Further detail concerning the driving circuit unit 40, the power source circuit unit 41, the delay circuit unit 43, and the driving trigger pulse generation unit 44 can be found in Japanese Patent Application No. 3-306106.

The ultrasonic wave treatment section of FIG. 10 further includes: an ultrasound imaging device 38 for obtaining the ultrasound tomographic images from the ultrasound imaging data collected by the ultrasonic wave probe 36; a digital scan converter (DSC) 39 for superposing the focal point 6 and the incidence route of the intense ultrasonic waves applied, a heated region on the tumor 7 and other information supplied from the control circuit unit 42 over the ultrasound tomographic images obtained by the ultrasound imaging device 38; a CRT display 37 for displaying the display image obtained by the DSC 39; and an image data input device 45 for inputting the image data to be supplied to the control circuit unit 42 from the displayed image displayed by the CRT display 37 by using a light pen device 49.

Here, the control circuit unit 42 can calculate the heated region on the tumor 7 in approximation from the positions and shapes of the focal point 6, the fluid equation, and the thermal absorption coefficients of the patient 3. The heated region can be displayed in different color from that used for a case of lithotriptor, in order to prevent the excessive heating. The CRT display 37 may also display the tomographic images obtained by the CT section as in the third embodiment described above.

Figure 11:
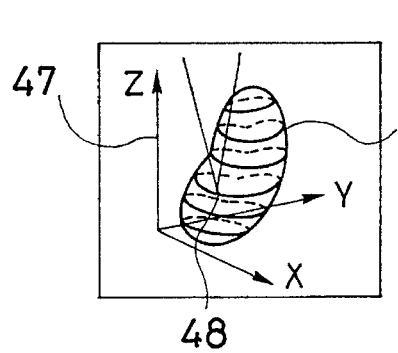
FIG. 11A is an illustration of an exemplary display to be used in the ultrasonic wave medical treatment apparatus of FIG. 10.
FIG. 11B is an illustration of contours of a tumor to be used in constructing a three-dimensional image information in the exemplary display of FIG. 11A.
Figure 11:
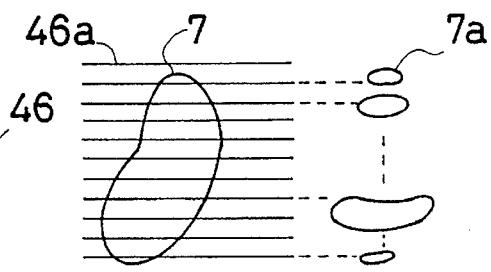

More specifically, as shown in FIG. 11A, the CRT display 37 can display the three-dimensional image information 46 on the tumor 7 obtained from either the ultrasound tomographic images obtained by the ultrasound imaging device 38 or the CT section, along with the three-dimensional coordinate frame 47 and the heated region 48 calculated by the control circuit unit 42. Here, in order to obtain the three-dimensional image information 46, each two-dimensional tomographic image on each imaging slice plane 46a obtained by the ultrasound imaging device 38 or the CT section is displayed on the CRT display 37 and the contour 7a of the tumor 7 to be treated on each imaging slice plane 46a is inputted into the control circuit unit 42 by using the image data input device 45 and the light pen device 49, and then the three-dimensional image information 46 is calculated at the control circuit unit 42 by integrating the inputted contours 7a. Further detail of the manner of obtaining the three-dimensional image information 46 can be found in Japanese Patent Application Laid Open No. 61-209643.

Figure 12A:
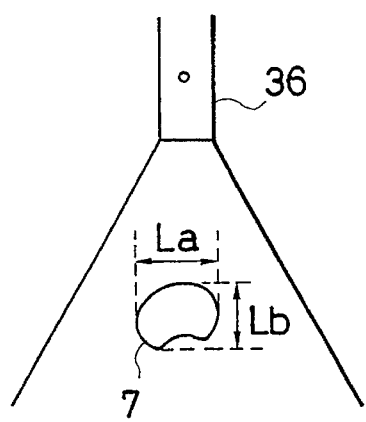
FIG. 12A and FIG. 12B are diagrammatic illustration of measurements of maximum lengths in three orthogonal directions to be utilized in obtaining an alternative three-dimensional image information to be displayed in the ultrasonic wave medical treatment apparatus of FIG. 10.
Figure 12B:
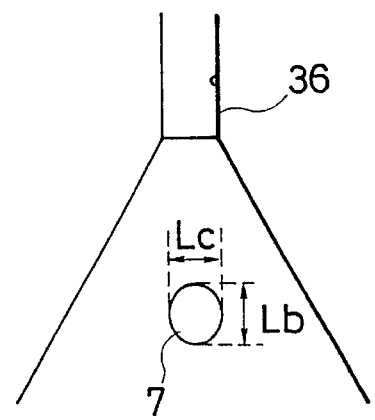
Figure 12C:
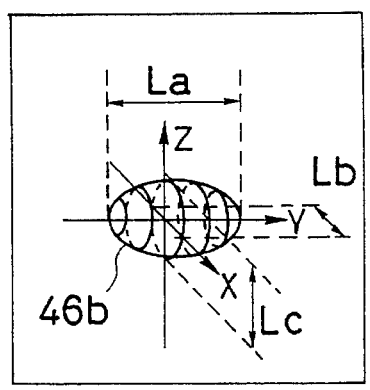
FIG. 12C is an illustration of the alternative three-dimensional image information to be displayed in the ultrasonic wave medical treatment apparatus of FIG. 10 obtained from the measurements made in FIG. 12A and FIG. 12B.

Alternatively, the CRT display 37 may display an ellipsoidal three-dimensional image information 46b shown in FIG. 12C, obtained by measuring the maximum lengths La, Lb, and Lc along the x, y, and z coordinate axes of the tumor 7 as indicated in FIG. 12A and FIG. 12B, and then calculating an ellipsoid 46b having approximately equivalent volume as the tumor 7 at the control circuit unit 42 according to the measured lengths La, Lb, and Lc.

Now, in this fifth embodiment, the application of the intense ultrasonic waves from the phased array ultrasonic wave applicator 30 is carried out in the following procedure designed to reduce the loss of the acoustic energy due to the cavitation.

First, as shown in FIG. 13A and FIG. 13B, the tumor 7 to be treated is divided along x, y, and z coordinate axes into a plurality of cells, each of which having thicknesses $\Delta dx$, $\Delta dy$, and $\Delta dz$ along the x, y, and z coordinate axes, respectively. Here, the thicknesses Δdx, Δdy, and Δdz of each cell are determined according to the size of the focal point 6 of the intense ultrasonic waves to be applied and the thermal absorption coefficient of the patient 3 such that the sufficient heating effect can be achieved at each cell by the application of the intense ultrasonic waves in the procedure described below. Here, the size of each cell is set to be slightly smaller than the size of the focal point 6 of the intense ultrasonic waves to be applied, in order to ensure that the application of the intense ultrasonic waves to the entire cell. Also, the thickness Δdz is usually set to be larger than the thicknesses Δdx and Δdy.

Then, the intense ultrasonic waves from the phased array ultrasonic wave applicator 30 are applied to each divided cell by sequentially shifting the focal point 6 of the intense ultrasonic waves according to the predetermined order such as that indicated in FIG. 14 for example.

Namely, according to the order indicated in FIG. 14, the cell labelled 1 in FIG. 14 is shot first, the cell labelled 2 in FIG. 14 is shot next, and so on. This order is devised to make the successive positions of the focal point 6 as far distanced from each other as possible throughout, so as to minimize the influence due to the cavitation.

Here, the intense ultrasonic waves are not applied at those cells which do not cover any part of the tumor 7 so that the undesirable damaging of the normal tissue can be prevented.

Also, the shifting of the focal point 6 can be realized either by a phase control of the phased array ultrasonic wave applicator 30 by the delay circuit unit 43 or by a mechanical control of the physical positions of the phased array ultrasonic wave applicator 30.

It is to be noted here that, each cell may be further divided into sub-cells such that the focal point 6 of the intense ultrasonic waves are shifted in units of these subcells, if desired.

Thus, according to this fifth embodiment, in addition to the advantages of the first or second embodiment described above, it becomes possible to reduce the influence due to the cavitation, so that the accuracy and the efficiency in the ultrasonic wave treatment can be improved.

It is further to be noted here that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An ultrasonic medical treatment apparatus, comprising:
   ultrasonic wave applicator means for applying ultrasonic waves to an object to be treated;
   non-ultrasonic computed tomography means for obtaining three-dimensional image information of the object to be treated;
   focal point control means for changing a position of a focal point of the ultrasonic waves applied by the ultrasonic wave applicator means without changing a view field of the computed tomography means;
   calculating means for determining the position of the focal point changed by the focal point control means in the three-dimensional image information obtained by the computed tomography means; and
   display means for displaying the three-dimensional image information obtained by the computed tomography means in superposition with the focal point at the position determined by the calculation means.

2. The apparatus of claim 1, wherein the computed tomography means comprises a nuclear magnetic resonance imaging device taking T2 weighted tomographic images before and after an application of the ultrasonic waves by the ultrasonic wave applicator means, the calculation means calculates a difference image between the T2 weighted tomographic images taken by the computed tomography means before and after the application of the ultrasonic waves by the ultrasonic wave applicator means, and the display means displays the difference image calculated by the calculation means.

3. The apparatus of claim 1, wherein the computed tomography means comprises a nuclear magnetic resonance imaging device for also taking chemical shift data before and after an application of the ultrasonic waves by the ultrasonic wave applicator means, the calculation means also calculates a difference image between the chemical shift data taken by the computed tomography means before and after the application of the ultrasonic waves by the ultrasonic wave applicator means, and the display means also displays the difference image calculated by the calculation means.

4. The apparatus of claim 1, wherein the display means displays an incidence route of the ultrasonic waves applied by the ultrasonic wave applicator means in superposition to the three-dimensional image information.

5. The apparatus of claim 1, further comprising:
   ultrasonic wave probe means, provided in conjunction with the ultrasonic wave applicator means, for collecting ultrasonic wave image data of the object to be treated; and
   ultrasound tomographic imaging means for obtaining ultrasound tomographic images of the object to be treated from the ultrasonic wave image data collected by the ultrasonic wave probe means, wherein the display means displays the ultrasound tomographic images obtained by the ultrasound tomographic imaging means.

6. The apparatus of claim 5, wherein the display means displays a slice region currently scanned by the ultrasonic wave probe means in superposition to the three-dimensional image information.

7. The apparatus of claim 5, wherein the computed tomography means obtains two-dimensional tomographic images of the object to be treated, and the display means displays the ultrasound tomographic images obtained by the ultrasound tomographic imaging means in real time, along with corresponding views of the two-dimensional tomographic images obtained by the computed tomography means.

8. The apparatus of claim 1, wherein the computed tomography means comprises a nuclear magnetic resonance imaging device, and the apparatus further comprising endocavitary probe means to be inserted into a body cavity of the object to be treated, containing an RF coil for applying RF pulses and collecting nuclear magnetic resonance signals to be used by the computed tomography means.

9. The apparatus of claim 8, wherein the endocavitary probe means includes a temperature sensor means for measuring temperature at a position of the endocavitary probe means and intensity sensor means for measuring intensity of the ultrasonic waves applied by the ultrasonic wave applicator means at a position of the endocavitary probe means.

10. The apparatus of claim 1, wherein the focal point control means sequentially shifts the focal point of the ultrasonic waves among divided portions of the object to be treated in an order in which no two successive positions of the focal point are located at adjacent ones of the divided portions.

11. A method of ultrasonic medical treatment, comprising the steps of:

applying ultrasonic waves to an object to be treated from an ultrasonic wave applicator device;

obtaining three-dimensional image information of the object to be treated by a non-ultrasonic computed tomography device;

changing a position of a focal point of the ultrasonic waves applied at the applying step without changing a view field of the computed tomography device;

determining the position of the focal point changed at the changing step in the three-dimensional image information obtained by the computed tomography device; and displaying the three-dimensional image information obtained by the computed tomography device in superposition with the focal point at the position determined at the determining step.

12. The method of claim 11, wherein the computed tomography device comprises a nuclear magnetic resonance imaging device, and the method further comprising the steps of:

taking T2 weighted tomographic images by the nuclear magnetic resonance imaging device before and after an application of the ultrasonic waves at the applying step;

calculating a difference image between the T2 weighted tomographic images taken by the nuclear magnetic resonance imaging device before and after the application of the ultrasonic waves at the applying step; and displaying the difference image calculated at the calculating step.

13. The method of claim 11, wherein the computed tomography device comprises a nuclear magnetic resonance imaging device, and the method further comprising the steps of:

taking chemical shift data by the nuclear magnetic resonance imaging device before and after an application of the ultrasonic waves at the applying step;

calculating a difference image between the chemical shift data taken by the nuclear magnetic resonance imaging device before and after the application of the ultrasonic waves at the applying step; and displaying the difference image calculated at the calculating step.

14. The method of claim 11, wherein at the displaying step, an incidence route of the ultrasonic waves applied at the applying step is also displayed in superposition to the three-dimensional image information.

15. The method of claim 11, further comprising the steps of:

collecting ultrasonic wave image data of the object to be treated by ultrasonic wave probe means;

obtaining ultrasound tomographic images of the object to be treated by ultrasound tomographic imaging means from the ultrasonic wave image data collected by the ultrasonic wave probe means; and displaying the ultrasound tomographic images obtained by the ultrasound tomographic imaging means.

16. The method of claim 15, wherein at the step of displaying the three-dimensional image information, a slice region currently scanned by the ultrasonic wave probe means is also displayed in superposition to the three-dimensional image information.

17. The method of claim 15, further comprising the steps of:

obtaining two-dimensional tomographic images of the object to be treated by the computed tomography device; and displaying the ultrasound tomographic images obtained by the ultrasound tomographic imaging means in real time, along with corresponding views of the two-dimensional tomographic images obtained by the computed tomography device.

18. The method of claim 11, wherein the computed tomography device comprises a nuclear magnetic resonance imaging device, and the method further comprising the step of inserting endocavitary probe means into a body cavity of the object to be treated, the endocavitary probe means containing an RF coil for applying RF pulses and collecting nuclear magnetic resonance signals to be used by the computed tomography device at the step of obtaining the three-dimensional image information.

19. The method of claim 18, further comprising the steps of:

measuring temperature at a position of the endocavitary probe means by temperature sensor means provided on the endocavitary probe means; and measuring intensity of the ultrasonic waves applied at the applying step at the position of the endocavitary probe means by intensity sensor means provided on the endocavitary probe means.

20. The method of claim 11, wherein at the changing step, the focal point of the ultrasonic waves is sequentially changed among divided portions of the object to be treated in an order in which no two successive positions of the focal point are located at adjacent ones of the divided portions.

* * * * *

UNITED STATES PATENT AND TRADEMARK OFFICE
CERTIFICATE OF CORRECTION

PATENT NO. : 5,485,839
DATED : January 23, 1996
INVENTOR(S) : Satoshi AIDA, et al.

It is certified that error appears in the above-indentified patent and that said Letters Patent is hereby corrected as shown below:

On the title page, Item [73], the Assignee, should read:

--Kabushiki Kaisha Toshiba, Kawasaki, Japan--

Signed and Sealed this

Thirtieth Day of July, 1996

Attest:

BRUCE LEHMAN

*Attesting Officer*     *Commissioner of Patents and Trademarks*